United States Patent [19]

Piet

[11] Patent Number: Plant 5,682

[45] Date of Patent: Mar. 4, 1986

[54] CAMELLIA CHRYSANTHA OLYMPIC GOLD

[76] Inventor: Meyer Piet, 15430 Proctor Ave., City of Industry, Calif. 91747

[21] Appl. No.: 613,725

[22] Filed: May 24, 1984

[51] Int. Cl.[4] ..... A01H 5/00

[52] U.S. Cl. ..... Plt./60

[58] Field of Search ..... Plt./60

*Primary Examiner*—Robert E. Bagwill

*Attorney, Agent, or Firm*—James E. Brunton

[57] ABSTRACT

A new and distinct type of Camellia Chrysantha raised from a single seed originating in China and having a true yellow-colored flower.

1 Drawing Figure

BACKGROUND OF THE INVENTION

1. Field of the Invention

The present invention relates to a new and distinct type of Camellia chrystantha, which was raised by me from a single seed sent to me from China via Japan. Camellia chrysantha is a true yellow colored camellia species, and the flower which first bloomed for me on Feb. 1, 1984 is the first true yellow color camellia flower to bloom in the United States and possibly Japan.

The 1984 Olympic Games are being held in the Los Angeles area, therefore I am naming by my new seedling "Olympic Gold".

2. Discussion of the Prior Art

The search for a yellow camellia started about 140 years ago. Robert Fortune, renowned botanical collector, tried to obtain a yellow color camellia from China without success (See *Wanderings in China,* published 1847). Later in his travels he found an anemone-formed flower with outer petals of a French White and inner ones of a Primrose Yellow, subsequently, named C. Jaune, from the French word for yellow. The late Ralph Peer, a camellia collector, rediscovered C. Jaune and grew it in the United States of America. I obtained a scion of C. Jaune from the Peer collection and was very disappointed in the flower as there was only a very light yellow cast in the center of the flower. Articles in *Camellia Review* (October 1958, page 14; and February 1977, page 13) make reference to a yellow-flowered seedling "Tutcheria" that Mr. E. C. Tourje bloomed from seed imported from Hong Kong. This plant, which never produced more than 5 flowers, was lost (died) before any seed or additional plants could be established.

Other renowned botanists have continued to obtain material from China, India, Japan, etc., but in every case the flower bloomed white, or white with a very pale yellow cast in the petaloids.

There are several *C. Japonica* that are white with a pale yellow cast, such as Brushfield Yellow, Botanuki (yellow cast, *C. Rusticanna*), and Ki Kirata, a Higo type flower. This group of flowers is very disappointing as the yellow is basically in the base of the petaloids and subsequently is more a reflection of yellow than a true yellow color.

For approximately 12 years I have been corresponding and exchanging plant materials and literature with Yoshiaki Andoh, one of the foremost camellia enthusiasts in Japan. In early 1980 Mr. Andoh let it be known to me that it could be possible to obtain material of the true yellow Camellia chrysantha from China.

I quote from his various correspondence:

Mar. 3, 1980

"Regarding C. Chrysantha, as my plants have not bloomed yet, I am afraid that I cannot send you pollen of them now. Actually, I recently obtained its scions from the Peoples Republic of China and did only two graftings. When they grow big enough to be cut off scions, I will surely send its scions to you first of all."

"In compensation for it, I am separately sending you today seeds of the following species:"

"1. C. Chrysantha Macrophilla (the largest seed)"

Apr. 10, 1980

"I am pleased to learn that the three species seeds I sent you reached in good condition, and it is my very pleasure to be able to share the hope with you to see beautiful flowers."

"Many people misunderstand that I have plenty of scions or seeds of C. Chrysantha and ask me for them, but actually I recently obtained a few scions as I told you before, and I cannot comply with all of their request. However, if I obtain the pollen of C. Chrysantha or seeds or scions of other rare species, I sill surely send some to you, a camellia magician, first of all."

Jan. 24, 1981

"I would like to help you with hybridizing yellow camellia with pleasure, however, by some reason or other my Chinese friend did not send the pollen of C. chrysantha this time. Now, it is quite hopeless to receive some pollen for you as the flower season of it has over. It really is a pity that you and I have to wait until our own young plants do produce the pollen. The trouble is that too many enthusiasts in all regions of the world make a fuss giving an imputus to Chinese. This must be the reason why they decided to keep the materials from escape in their own land."

Mar. 7, 1981

"Duly received your letter of January 29, I am very sorry for being unable to meet your expectation right away, because your estimate for my collection of recent introduction from China seems to be too over. Speaking the truth, my collection has been so unluck from the start."

"The scion of C. chrysantha being the first material exported from China behind the bamboo curtain and grafted in September 1979 has received damage during our stay in Kyoto for the International Convention in the late March 1980. Since then the very plant has stopped to grow. The enclosed picture No. 1 shows its present condition. Also in the late January 1980, I succeeded to import some seeds of C. Chrysantha collected from its native forest in Kuanghsi. The seed I sent to you was one of them."

The real cuttings of C. chrysantha obtained from China were lost, and to this date even Mr. Andoh has not bloomed his seedlings of C. chrysantha as the flower buds that appeared for the last two seasons dropped off before blooming. The single seed sent to my by Yoshiaki Andoh was germinated successfully, then allowed to grow for one season. The plant started to look sick and was showing no new growth, so I decided to graft it. I selected Special Camellia understock of Species Granthamiana, C. irrawadiensis, C. Sasanqua and C. Japonica.

BRIEF DESCRIPTION OF THE DRAWINGS

The drawing is an actual color photograph of the flower of the plant of my invention.

DESCRIPTION OF THE INVENTION

The present plants (3) which have bloomed this season are grafted on Camellia Granthamiana and Sasanqua understock and are approximately 7 feet tall with a total of 14 flowers that have bloomed.

1. Parentage: Chance seedling of Camellia chrysantha.
2. Propagation: Hold its distinguishing characteristics through succeeding propagations by grafting.
3. Blooming habits: New buds can be seen as early as July or August. these slowly grow larger, blooming occurred on February 1 and flowers continued to bloom until the end of March.
4. Bud:
   - A. *Size.*—Swells to approximately $\frac{3}{4}$ inch (19 mm) before opening.
   - B. *Form.*—Almost true round in shape, opening in a cup shape.
   - C. *Color.*—Empire yellow #603 with a blush red in center of the back petals.
   - D. *Sepals.*—Usually 3 petaloids, very smooth, triangular form just before opening.
   - E. *Calyx.*—Round, color as noted above, relatively smooth, no sign of brown color or a hard shell.
5. Bloom:
   - A. *Size.*—When fully open $1\frac{3}{4}$ to $2\frac{1}{4}$ inches in diameter (4.4 to 5.7 CM).
   - B. *Borne.*—Singly, along the stem adjacent to a leaf, not on the branch terminals. Usually protrude approximately $\frac{1}{2}$ inch (12.7 MM) similar to species *C. irrawadiensis* and *C. sinenis.*
   - C. *Form.*—When first petal opens, cup or bell form, when fully open, semi-double, 2 rows of approximately 10 petals.
   - D. *Color.*—Does not vary, remains yellow, Empire Yellow #601/1, when opening and thereafter. Does not show any signs of white.
   - E. *Bloom.*—Falls in one piece from the plant.
6. Petals:
   - A. *Texture.*—Thick, soft, inside and outside, satiny texture, outside of petals look like they have been heavily waxed.
   - B. *Shape.*—Circular or slightly elliptical in shape.
   - C. *Arrangement.*—Semi-double, two rows of approximately 5 petals in each row overlapping.
   - D. *Lasting qualities.*—Excellent, on plant 5 to 6 days. Spent flower drops in one piece, ovary, styles and stigmas remain on the plant with the calyx, which then closes when pollenated.
7. Reproductive organs:
   - A. *Stamens.*—Small, basically "X" shape, large quantity for flower size, yellow in color.
   - B. *Anthers.*—Approximately $\frac{3}{8}$ to $\frac{1}{2}$ inches long (9.5 to 12.7 MM), yellow in color.
   - C. *Pollen.*—Yellow in color.
   - D. *Styles.*—3 or 4 grouped together in center of flower.
   - E. *Ovaries.*—All enclosed in Calyx.
8. Fruit:
   - A. *Has not seeded yet.*—Probably due to the young age and first flowering of the plant.
   - B. *Original seed.*—3 Cotyledons, which is very unusual as all other Camellia have 2 cotyledons.
9. Plant:
   - A. *Form.*—Very tall, very bushy, all branches upright.
   - B. *Growth.*—Vigorous new growth, 3 or 4 cycles per year.
   - C. *Foliage.*—(1) Size — Large, 4 to 6 inches long (10.2 to 15.2 CM) 2 to $2\frac{3}{4}$ inches wide (5.1 to 7.0 CM). (2) Quality — Extremely abundant. (3) Color — New foliage — a beautiful black-red color when it opens. Old foliage, an excellent rich dark green, lower surface of leaves lighter green than the upper surface. (4) Lanceolate, terminating to a point at the end. (5) Veins — Very prominent similar to foliage of species *C. Granthamiana.* (6) Edge — Finely serrated.
   - D. *Wood.*—Light gray color.

I claim:

1. A new and distinct species of camellia plant as shown and described, characterized particularly by its unique flower which has a true yellow color.

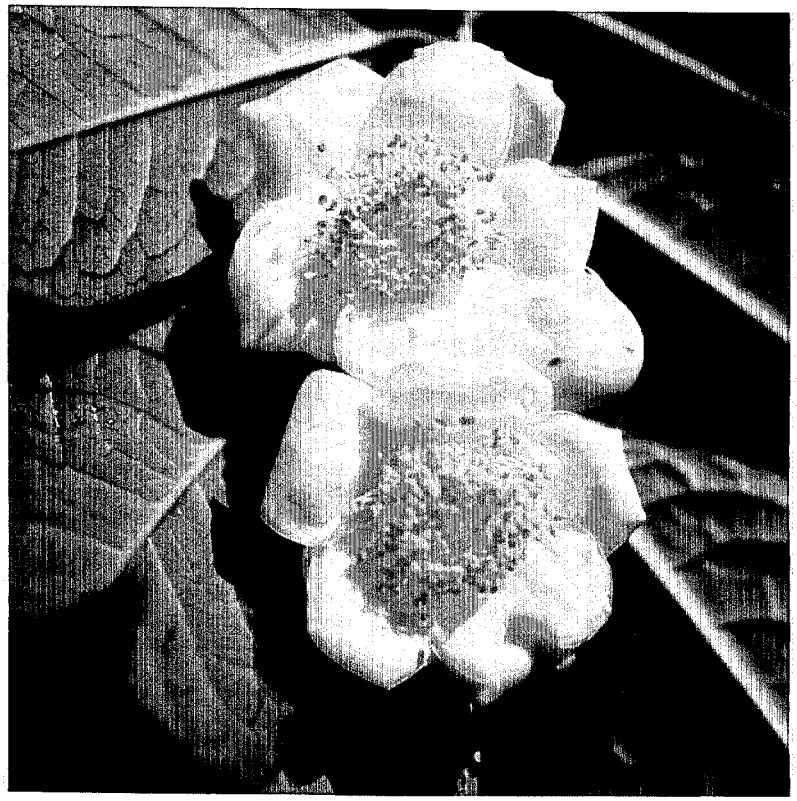

* * * * *